Figure 1:
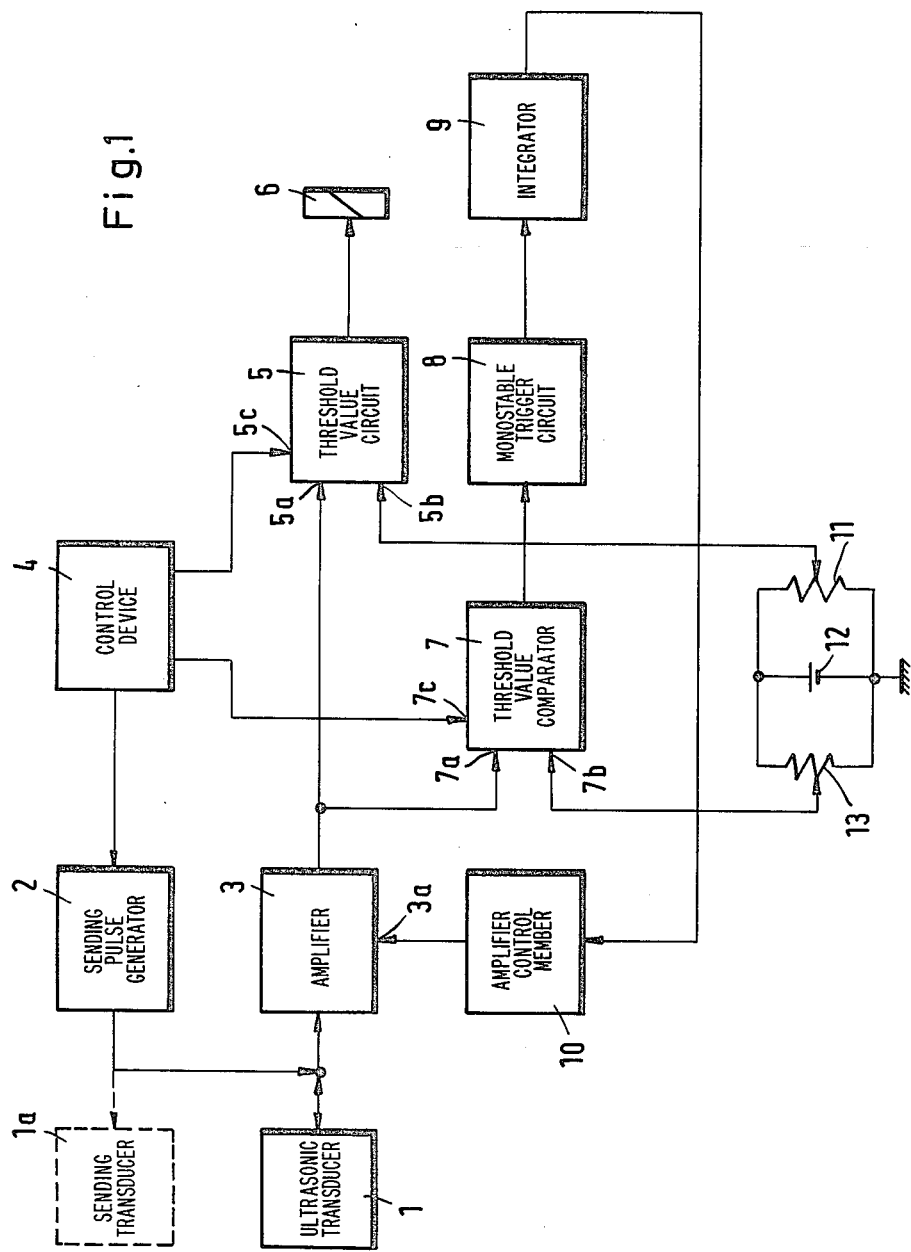

United States Patent [19]
Wetzel

[11] 4,202,049
[45] May 6, 1980

[54] ULTRASONIC-FILLING POSITION LIMIT SWITCH OPERATING ACCORDING TO THE ECHO PRINCIPLE

[75] Inventor: Gustav Wetzel, Loerrach, Fed. Rep. of Germany

[73] Assignee: Endress u. Hauser GmbH u. Co., Maulburg, Fed. Rep. of Germany

[21] Appl. No.: 944,168

[22] Filed: Sep. 20, 1978

[30] Foreign Application Priority Data

Sep. 27, 1977 [DE] Fed. Rep. of Germany ....... 2743409

[51] Int. Cl.² .......................... G01S 9/66; G01S 7/66
[52] U.S. Cl. ........................................ 367/96; 367/98; 367/908; 73/290 V; 340/621
[58] Field of Search ..................... 340/1 L, 1 R, 621; 343/7 AG; 73/290 V

[56] References Cited
U.S. PATENT DOCUMENTS

| | | | |
|---|---|---|---|
| 2,711,531 | 6/1955 | Murdock | 343/7 AG |
| 3,407,398 | 10/1968 | Stearn | 340/1 L |

Primary Examiner—Richard A. Farley
Attorney, Agent, or Firm—Gerald J. Ferguson, Jr; Joseph J. Baker

[57] ABSTRACT

An ultrasonic filling position limit switch having disposed in the container at the full level thereof, at least one ultrasonic transducer for sending out ultrasonic pulses and for receiving echo pulses reflected off the opposite container wall. An amplifier of the electric output signals of the transducer is connected to a threshold limit switch which provides an output signal when the amplifier output signal exceeds a predetermined threshold value. The amplifier output is fed back to an amplifier control input by means of an amplifier control circuit which seeks to maintain the amplifier output signal at an adjustable constant nominal value. A control device blocks the control circuit for the duration of time in each sending period required for the sending out of the ultrasonic sending pulses and for receiving the echo pulses.

3 Claims, 2 Drawing Figures

ULTRASONIC-FILLING POSITION LIMIT SWITCH OPERATING ACCORDING TO THE ECHO PRINCIPLE

The invention relates to an ultrasonic filling position limit switch operating according to the echo principle having arranged in the container at the filling level to be attained at least one ultrasonic transducer for sending out ultrasonic pulses and for receiving echo pulses reflected off the opposite container wall, an amplifier for the electric output signals of the ultrasonic transducer connected to the ultrasonic transducer, and a threshold limit switch connected to the amplifier output which supplies an output signal when the amplifier output signal exceeds a predetermined threshold value.

With ultrasonic filling position limit switches of this type the ultrasonic transducer, which is periodically excited by electric high frequency pulses, sends out ultrasonic pulses in a horizontal direction. When at the level of the ultrasonic transducer there is located a medium, which is suitable for transmission of ultrasonic waves, these waves travel to the opposite container wall where they are reflected so that an echo pulse returns, which is received and converted back into an electric signal by the ultrasonic transducer used in sending, or its own receiver transducer arranged beside the former. To ascertain whether a predetermined filling position has been exceeded or not reached, depends upon the fact that high frequency ultrasonic waves are heavily attenuated in air.

When there is air in the container at the level of the ultrasonic transducer, no echo is directly received by the ultrasonic transducer from the opposite container wall. If on the other hand there is in the container at the level of the ultrasonic transducer a filling material, particularly liquids, in which ultrasonic waves of these high frequencies are able to spread out, a relatively strong echo is received. The reception or non reception of an echo pulse will therefore indicate whether the filling level in the container is above or below the height at which the ultrasonic transducer is located in the container.

The echo amplitude is determined, amongst others, by the ultrasonic transducer used, the method of coupling the transducer to the container, the material from which the container is made, the container diameter and the filling liquid. The echo travel time is determined by the container diameter and the speed of sound in the filling liquid. The speed of sound in the medium again depends upon various factors, particularly the type of filling liquid and its temperature. For a given case of application it is possible to determine a time interval in which, in consideration of all deviations to be expected, an echo pulse directly reflected off the opposite container wall must arrive at the ultrasonic transducer. Preferably, the reception arrangement in each sending period is activated only during this time interval, known as the 'gate time', and during the remaining time is blocked. This ensures in particular that the receiving device during the sending out of the sending pulses, is inactive.

The electrical signal given off by the ultrasonic transducer as a result of the echo pulses is amplified by the amplifier and so long as it appears within the gate time and exceeds the predetermined threshold value, it is converted by the threshold value circuit into a control signal which can be used for indicating and/or triggering control processes.

As a result of the constantly present interference level in the container it may be possible that the ultrasonic transducer will give off output signals even when the filling position lies below the critical value to be ascertained. When such interference signals appear during the gate time, they must not result in the giving off of a control signal, because this would indicate a faulty filling position. For this reason either the threshold value or the amplification of the amplifier, in the case of an empty container, is so adjusted that in the presence of the interference level no control signal is produced. On the other hand, the adjustment must take place in such a way that with a full container the weakest echo available must still result in the giving off of a control signal, since otherwise likewise a faulty reading of the filling position will be indicated. This adjustment must in each case be carried out at the place of fitting, which requires careful measuring by a skilled person. However, when after some time as a result of changed operating conditions the interference level and/or the echo amplitude is changed, the adjustment is not correct anymore, a fact which can lead to a malfunction of the filling position limit switch.

It is the object of the invention to provide an ultrasonic filling position limit switch of the above-named type in which without complicated adjustments and changing operating conditions it is possible to substantially eliminate malfunctions caused by interference signals or a non-reception of the useful echo pulses.

According to the invention this is achieved in that the amplifier output is fed back to an amplifier control input by means of an amplifier control circuit which seeks to maintain the amplifier output signal at an adjustable constant nominal value, and a control device which blocks the control circuit for the duration of time in each sending period required for the sending out of the ultrasonic sending pulses and for receiving the echo pulses.

In the ultrasonic filling position limit switch according to the invention the interference signal at the output of the amplifier is kept constant to a predetermined threshold value; by blocking the amplifier control circuit it is ensured that the amplifier control takes place exclusively as a result of the interference signal level and that the sending pulses and received useful echos do not enter the control. If the nominal value is applied by sufficiently small amount below that of the threshold value applied to the useful echo coverage, it is ensured that on the one hand no interference signals are evaluated as useful echos, and that on the other hand even weak useful echos are picked up with certainty, So long as they exceed the interference level by a small amount. This optimum operating condition is automatically effected during the installing of the apparatus and is automatically maintained during the changing of the interference level.

Preferably the control device clears the amplifier control circuit in each sending period between the time interval allocated for the sending out of the sending pulses and the time interval for receiving the echo pulses. This measure ensures that the interference level appearing just before the echo is received is decisive for the amplification control.

In a preferred embodiment of the ultrasonic filling position limit switch according to the invention the amplification control circuit comprises an adjustable threshold value comparator connected with the output of the amplifier, which comparator gives off an output signal when the output signal of the amplifier exceeds a predetermined threshold value, as well as a monostable trip circuit responding to the output signal of the threshold value comparator and an integrator connected to the output of the monostable trip circuit, the output of the integrator acting upon an amplification control member.

Figure 2:
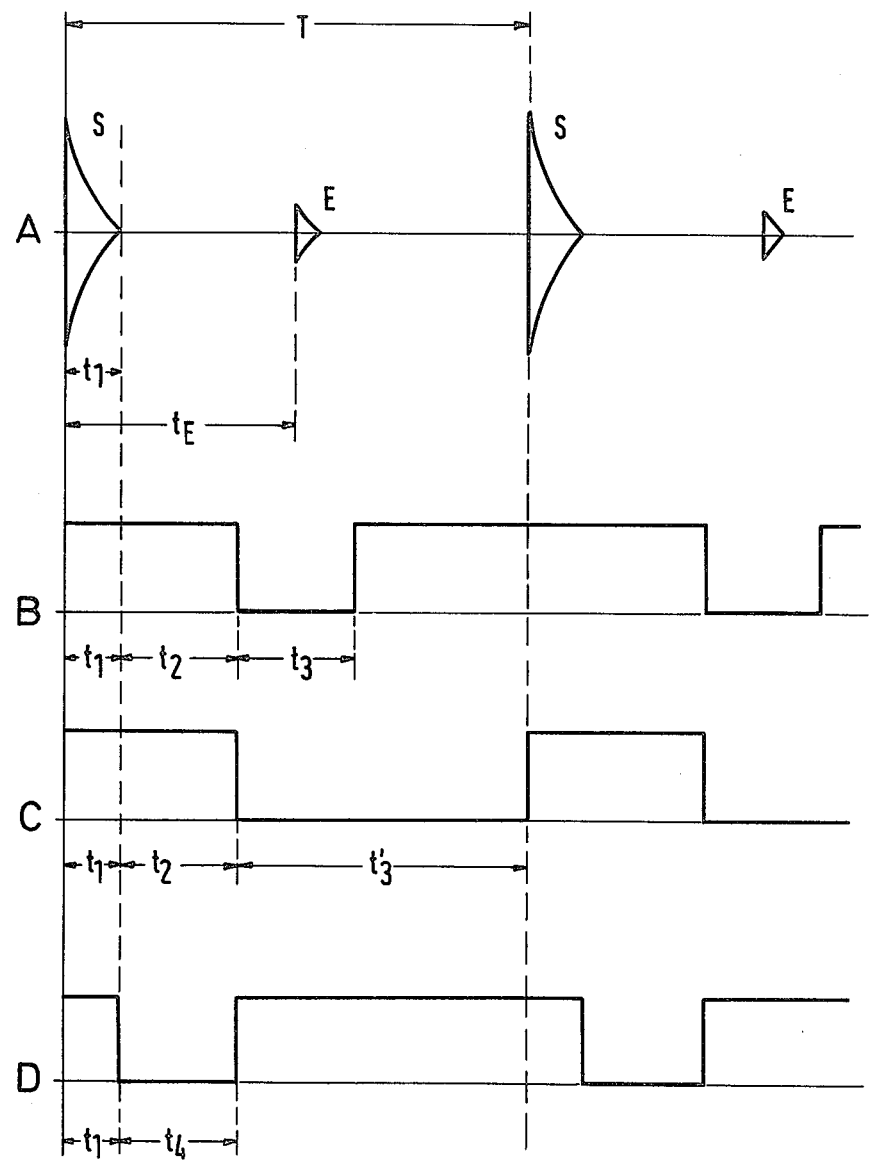

Further features and advantages of the invention will become obvious from the following description of an example of an embodiment described with the aid of drawings. The drawings show:

FIG. 1 the block diagram of an ultrasonic filling position limit switch according to the invention and FIG. 2 diagrams for explaining the operating characteristics of the ultrasonic filling position limit switch according to FIG. 1.

The ultrasonic limit switch shown in FIG. 1 comprises an ultrasonic transducer 1 which is arranged in the container, whose filling level is to be monitored, at the level of the critical filling position to be monitored. The ultrasonic transducer 1 is so constructed that it can operate as sending transducer for sending out ultrasonic pulses as well as receiver transducer for the reception of ultrasonic echo pulses. The ultrasonic transducer 1 on the one hand is connected with the output of a sending pulse generator 2 and on the other hand connected with the input of an amplifier 3. Optionally it is also possible to connect to the output of the sending pulse generator 2 a separate sending transducer 1a, as shown in FIG. 1 in broken lines; in this case the ultrasonic transducer 1 would only serve as receiver transducer, and the connection between the ultrasonic transducer 1 and the sending pulse generator 2 would be obsolete.

The operation of the ultrasonic limit switch is controlled by a control device 4, which is particularly responsible for inducing the sending pulse generator 2 to periodically release short high frequency sending pulses. The frequency of the sending pulses for example is in the range of above 1 Mhz.

The electrical sending pulses given off by the sending pulse generator 2 are converted by the ultrasonic transducer 1 (or by the separate sending transducer 1a) into ultrasonic pulses of the same frequency and beamed horizontally into the container.

The ultrasonic transducer 1 can receive echo pulses in the intervals between two successive sending pulses. It changes the echo pulses into electrical pulses which are fed back to the input of the amplifier 3 whose amplification is adjustable by applying a control signal to an amplification control input 3a. The output signal of the amplifier 3 is fed to one of the inputs 5a of a threshold value circuit 5, to the second input 5b of which a voltage determining the threshold value can be applied. The threshold value circuit 5 in addition has a control input 5c which is connected with an output of the control device 4. By applying a blocking signal to the control input 5c, the threshold value circuit 5 can be blocked. The threshold value circuit 5 is so arranged that the output produces a d.c. signal, while during the releasing time during which it is not blocked by a blocking signal applied to the control input 5c, a signal appears at input 5a which exceeds the threshold voltage applied to the input 5b. This d.c. signal can serve to indicate or release control processes, for example by exciting a relay 6 connected to the output of the threshold value circuit 5.

The output of the amplifier 4 is furthermore connected with the input 7a of a threshold value comparator 7 which has another input 7b to which is applied a voltage for determining the threshold value. The control input 7c of the threshold value comparator 7 is connected with the control device 4; by applying a blocking signal to the control input 7c it is possible to block the threshold value comparator 7.

The threshold value comparator 7 is so arranged that the output produces a signal when during its release time, in which it is not blocked by a blocking signal applied to the control input 7c, a signal appears at the input 7a which exceeds the threshold value voltage applied to the input 7b. To the output of the threshold value comparator 7 is connected a mono-stable trigger circuit 8 which is triggered by the output signal of the threshold value comparator 7. The pulse produced by the monostable trigger circuit 8 is fed to the integrator 9 whose output is connected with a control member 10 for determining the amplification of amplifier 3. The control member 10 for example may be a field effect transistor, whose control electrode is connected with the integrator 9.

The periodic control of the various components of the device according to FIG. 1 by the control device 4 can be seen from the time diagrams of FIG. 2. The diagram A shows the sending pulses s which are sent out by the ultrasonic transducer 1 within the space of sending period t. The sending pulses fade away after a time lapse t1. When a medium is in the container which permits the propagation of ultrasonic waves, after an echo travelling time tE, which is dependant upon the diameter of the container, speed of sound in the medium, an echo pulse E, which has been reflected off the opposite container wall, arrives at the ultrasonic transducer 1.

The diagram B shows the blocking signal applied from the control device 4 to the control input 5c of the threshold value circuit 5. Since for a given case, the point of time in which an echo pulse e can appear deviates only relatively slightly and can be precisely determined, the threshold value circuit 5 is opened only during a relatively short gate time t3, which begins only after the passing of a time interval t2 at the end of the sending time interval t1. The threshold value circuit 5 in other words evaluates only echo signals which are received during the gate time t3. If during this time interval an echo pulse E appears and which exceeds the threshold value adjusted at the input 5b, the threshold value circuit 5 gives off at the output a d.c. signal which indicates that the filling position in the container is above the level determined by the position of the ultrasonic transducer 1. When during the gate time t3 at the input of the threshold value circuit 5a no signal exceeding the threshold value appears, this will be taken as a sign that the filling position is below the level of the ultrasonic transducer 1.

As illustrated in diagram C, the gate time t3 can be increased by an amount corresponding to the sending out of the next send pulse s. This is possible since multiple echoes do not affect the function of the filling position limit switch.

Diagram D shows the blocking signal applied to the control input 7c of the threshold value comparator 7. As can be seen, the threshold value comparator 7 is released only during a time interval t4, which lies in the time interval t2 between the end of the send pulse and the beginning of the gate time t3 or t13 provided for evaluating the echo signal or, as indicated, is equal to the time interval t2. In this time interval no echo signal can appear at the output of the amplifier 3; this is utilised in the monitoring of the interference signal level.

When the maximum value of the interference signal appearing at the output of the amplifier 3 during the time interval t4 exceeds the threshold value applied to input 7b of the threshold value comparator 7, the threshold value comparator 7 gives off a signal at the output which triggers the mono-stable trigger circuit 8. The pulse given off by the monostable trigger circuit 8 is then integrated by the integrator 9. The integrator voltage controls the control member 10 in such a way that the amplification is reduced. As a result of the time constant of the control circuit caused by the integrator 9, the smaller amplification remains active until the next sending period.

When during the next sending period the interference signal at the output of amplifier 3 again exceeds the threshold value of the threshold value comparator 7, the monostable trigger circuit 8 is again released so that the integrator 9 integrates a further pulse; the integrated voltage thus again increases and the amplification is furthermore decreased.

If on the other hand, as a result of lowering the amplification, during the subsequent monitoring of the interference signal level during the time t4 in the subsequent sending period the maximum value of the interference signal remains below the adjusted nominal value, the monostable trigger circuit 8 is not released so that the voltage integrated by integrator 9 decreases. This increases amplification via the control member 10. This process is periodically repeated so that the amplification deviates about an average value determined by the nominal value and the interference signal level. The circuit components 7, 8, 9, 10 thus act as control circuit which seeks to maintain at a constant value the maximum values of the output signals of the amplifier 3 during the time intervals t4. The deviations from the average value can be kept small by a corresponding choice of the integration time constants. When the interference signal level changes, a new average value automatically appears for amplification, in which the interference signal at the output of amplifier 3 again has the same constant maximum value.

For adjusting the threshold value the input 5b of the threshold value circuit 5 may be connected with the tap of a potentiometer 11, which is connected to the reference voltage source 12. The input 7b of the threshold value comparator 7 is likewise connected with the tap of a potentiometer 13 which is connected to the same reference voltage source 12.

The potentiometer 13 is so adjusted that the interference signal during the release times t3 appearing at the output of the amplifier 3, in consideration of the largest deviations effected by the control, never reaches the threshold value adjusted by potentiometer 11 at the input 5b of the threshold value circuit 5. In all probability this will prevent that the threshold value circuit 5 during its release time t3 will respond to interference signals. Since this safety margin is maintained by the control even when changing the interference signal level, the amplifier 3 will always give the optimum amplification for evaluating the useful echo with regard to the interference signal level.

The production of the threshold value voltages applied to the inputs 5b and 7b by means of the voltage separators, which are connected to the same reference voltage source, has the additional advantage that deviations in the reference voltage act in the same way on the threshold value voltages adjusted to the threshold value circuit 5 and the threshold value comparator 7, so that the ratio of the threshold value voltages remains unchanged. No high demands are therefore made on the constancy of the reference value source 12.

I claim:

1. In an ultrasonic filling position limit switch having arranged in a container at the filling level to be attained at least one ultrasonic transducer for sending out ultrasonic pulses and for receiving echo pulses reflected off the opposite container wall, an amplifier for the electric output signals of the ultrasonic transducer connected to the ultrasonic transducer and a threshold limit switch connected to the amplifier output which supplies an output signal when the amplifier output signal exceeds a predetermined threshold value, the improvement that the amplifier output is fed back to an amplifier control input by means of an amplifier control circuit which seeks to maintain the amplifier output signal at an adjustable constant nominal value, and a control device which (a) blocks the control circuit for the duration of time in each sending period required for the sending out of the ultrasonic sending pulses and for receiving the echo pulses, (b) releases the amplifier control circuit during each sending period between the time interval provided for sending out the sending pulses and the time interval provided for receiving the echo pulses and (c) blocks the threshold limit switch during the sending out of the sending pulses and during the release time of the amplifier control circuit.

2. Ultrasonic filling position limit switch according to claim 1 where the amplifier control circuit contains an adjustable threshold value comparator connected with the output of the amplifier, which comparator produces an output signal when the output signal of the amplifier exceeds a predetermined threshold value, as well as a monostable trigger circuit responsive to the output signal of the threshold value comparator and an integrator connected to the output of the monostable trigger circuit, the output of the integrator acting upon an amplifier control member.

3. Ultrasonic filling position limit switch according to claim 2, characterised in that the threshold value of the threshold value comparator is adjusted to a nominal value which is slightly below the threshold value of the threshold limit switch.

* * * * *